United States Patent [19]

Karrer

[11] 4,029,649

[45] * June 14, 1977

[54] TERPENE ARYL ESTERS

[75] Inventor: Friedrich Karrer, Basel, Switzerland

[73] Assignee: Ciba-Geigy Corporation, Ardsley, N.Y.

[ * ] Notice: The portion of the term of this patent subsequent to Apr. 13, 1993, has been disclaimed.

[22] Filed: May 16, 1973

[21] Appl. No.: 360,853

Related U.S. Application Data

[63] Continuation-in-part of Ser. No. 190,307, Oct. 18, 1971, abandoned.

[30] Foreign Application Priority Data

Oct. 20, 1970 Switzerland ............... 15436/70
Aug. 23, 1971 Switzerland ............... 12321/71

[52] U.S. Cl. ............... 260/240 H; 424/278; 424/340; 260/348 R; 260/613 D
[51] Int. Cl.² ............... C07D 303/28
[58] Field of Search ............... 260/240 H, 613 D

[56] References Cited

UNITED STATES PATENTS 3,718,686  2/1973  Chodnekar et al. ........... 260/240 H
3,880,935  4/1975  Chodnekar et al. ........... 260/613 D
3,957,833  4/1976  Chodnekar et al. ........... 260/348 R Primary Examiner—John D. Randolph
Attorney, Agent, or Firm—Harry Falber; Frederick H. Rabin

[57] ABSTRACT

New terpene aryl ethers of the formula

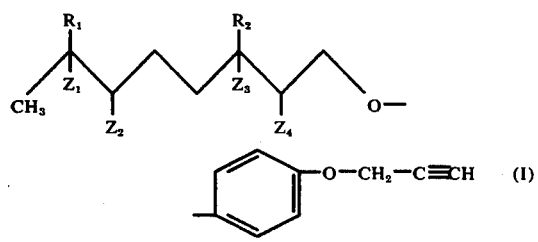

wherein
$Z_1$ and $Z_2$ together form a carbon-carbon-bond or together are an oxygen bridge,
$R_1$ and $R_2$ are each methyl or ethyl,
$Z_3$ and $Z_4$ together form a carbon-carbon-bond or are each hydrogen or
$Z_1$, $Z_2$, $Z_3$ and $Z_4$ are all hydrogen and their use for combating insects are disclosed.

6 Claims, No Drawings

TERPENE ARYL ESTERS

CROSS REFERENCE TO RELATED APPLICATIONS

This Application is a continuation-in-part of Patent Application Ser. No. 190.307, filed Oct. 18, 1971 now abandoned.

DISCLOSURE

The present invention relates to new terpene aryl ethers and their use for combating insects.

The new terpene aryl ether have the formula

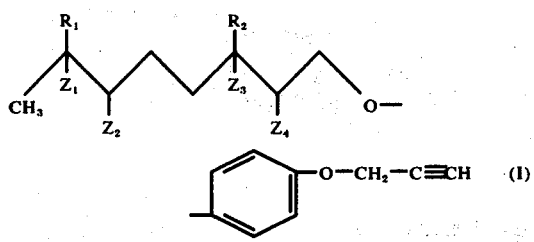

(I)

wherein $Z_1$ and $Z_2$ together form a carbon-carbon-bond or together are an oxygen bridge, $R_1$ and $R_2$ are each methyl or ethyl, $Z_3$ and $Z_4$ together form a carbon-carbon-bond or are each hydrogen or $Z_1$, $Z_2$, $Z_3$ and $Z_4$ are all hydrogen.

Preferred compounds on account on their activity are of the formula

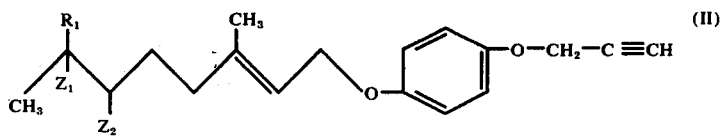

(II)

wherein $R_1$ is methyl or ethyl and $Z_1$ and $Z_2$ together form a carbon-carbon-bond or together are an oxygen bridge.

For the manufacture of compounds of the formula I takes place in fashion known per se by the following reactions, preferably with equimolecular quantities of the starting material; if desired, however, an excess of one or more of the reactants can be used:

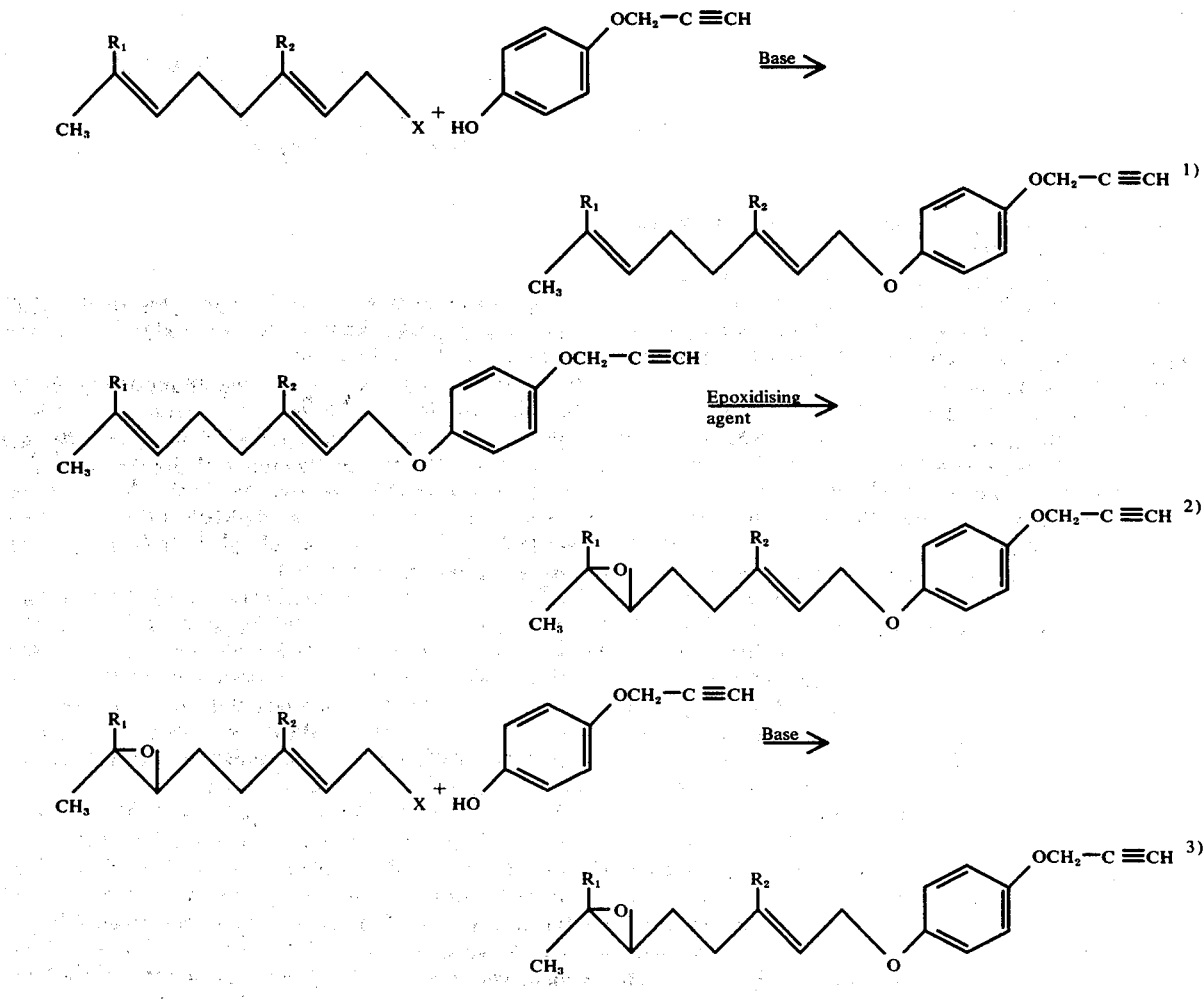

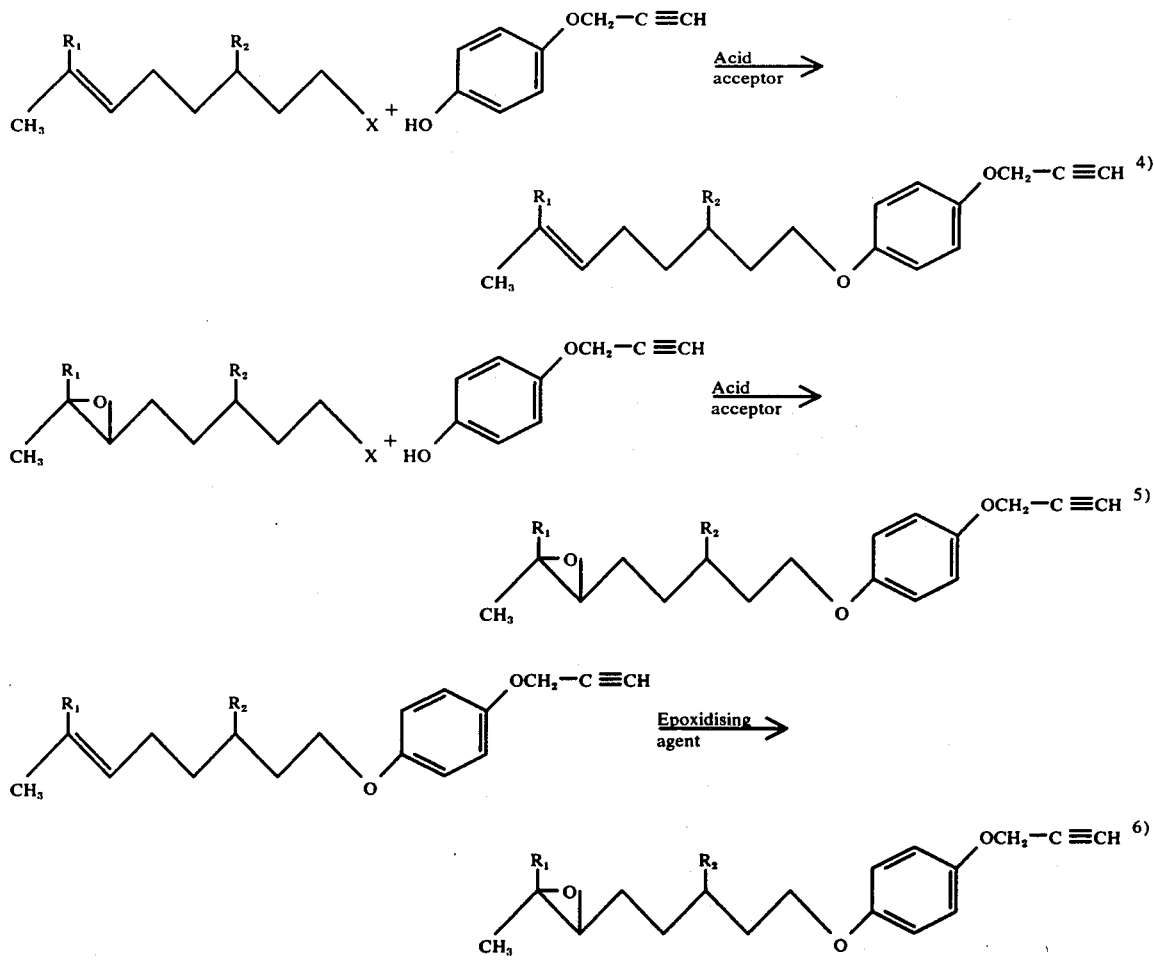

In these equations X is halogen, preferably chlorine or bromine. Reactions (1) and (3), i.e. the reactions with mixtures of geometrical isomers of the reactive allylic halides with the desired phenol are carried out in a solvent such as 1,2-dimethoxyethane, tetrahydrofurane, dioxane, dimethylformamide, dimethylsulfoxide, sulfolane or a dialkylether, preferably, however in 1,2-dimethoxyethane, by slow addition of an equivalent of an acid acceptor such as an alkali or alkaline earth hydroxide or alkali or alkaline earth carbonate, or alkali alkoxide or alkali hydride with stirring at room temperature and optionally with subsequent warming. The isolation of the terpene aryl ether then takes place by known techniques. Amongst alkalis there should be understood here particularly potassium and sodium and among alkaline earth metals calcium. Reactions (2) and (6), i.e. the transfer of the terpenoid arylether into their 6,7 derivatives are preferably carried out with cooling in an inert solvent medium such as for example a chlorinated hydrocarbon, with an epoxidising agent, for example a peracid. With the use of one more of peracid, then as a result of the steric factor predominantly the 6,7 epoxy derivative is formed. The 6,7 epoxy derivatives can also be obtained with N-bromosuccinimide in a mixture of water with a solvent such as tetrahydrofurane, 1,2-dimethoxyethane, dioxane, or tert.butanol in homogeneous or hetragenerous phase with subsequent treatment of the intermediary bromo hydrin which arises with an alkaline agent such as an alkali carbonate, alkali hydroxyide or an alkali alkoxide. Among alkalis particularly sodium and potassium are to be understood.

By the term peracid, there is to be understood predominantly low peralkane acids with 1–6 carbon atoms, e.g. peracetic acid, as well as aromatic peracids such as perbenzoic acid, monoperphthalic acid, and particularly m-chloroperbenzoic acid. As basic reagents for transforming a bromohydrin into 6,7 epoxy derivatives alkali carbonates, alkali hydroxydes, and alkali alkoxides can be used.

The reaction according to equation (4) i.e. the reaction for example of a non-allylic aliphatic halide with a desired phenol takes place preferably in the presence of at least 1 mol of an alkali or alkaline earth carbonate, as well as with or without a catalytic quantity of an alkali iodide in a solvent medium such as e.g. acetone, methylethylketone, or cyclohexanone between room temperatures and boiling temperature of the solvent used. The reaction can also take place with the aid of an alkali hydroxyde in a solvent, e.g. dimethylformamide, dimethylsulfoxide, sulfolane or 1,2-dimethoxyethane between 0° and 100° C. As further variation in the synthesis there should be mentioned the reaction of a 1-(4-hydroxy)-phenoxy-3,7-dialkyl-2,6-octa or nonadiene with a halo derivatives (in the presence of a base, e.g. a tertiary amine, alkali carbonate or alkali hydroxyde), to a phenol diether of the formulae III to IV.

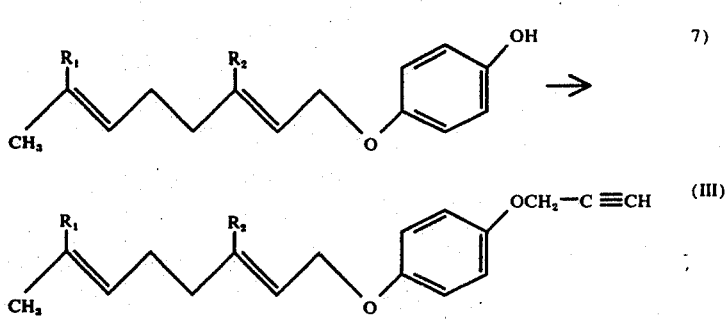

Analogously the 1-(4-hydroxy)-phenoxy-3,7-dialkyl-6-octene or 6-nonene compounds can be transformed to phenol diethers.

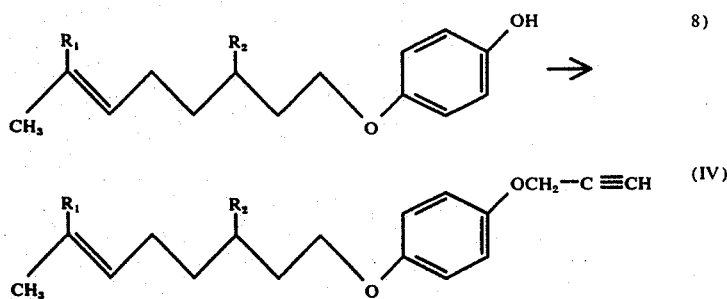

The so obtained phenyl diethers can then be transformed with an epoxidising agent in the cold in an inert solvent medium into the 6,7 epoxy derivative.

The substituents $R_1$ and $R_2$ (in reactions 1 to 8) have the meaning given for formula I.

In the manufacture of compound of formula I as a result of the alkyl halides used for the synthesis all possible geometrical isomers form. The compounds described are in the form of mixtures of the geometrical isomers which are obtained by the synthesis.

The active substances of formula I are suitable for combating most varied insects. In contrast to most previously known insecticides which rapidly kill, paralyse or drive away the animals working as contact or ingestion poisons, the active substances of formula I influence the development. The new terpenoid arylethers can be used above all for combating the following plant, stored product and hygiene insects of the order of families:

Orthoptera
  Acrididae
  Gryllidae
  Blattidae
Isoptera
  Kalotermitidae
Hemiptera
  Miridae
  Piesmidae
  Lygaeidae
  Phyrrhocoridae
  Pentatomidae
  Cimicidae
  Reduviidae
  Jassidae
  Eriosomatidae
  Lecaniidae
Coleoptera
  Carabidae
  Elateridae
  Coccinellidae
  Tenebrionidae
  Dermestidae
  Cucujiidae
  Chrysomelidae
  Curculionidae
  Scolytidae
  Scarabaeidae
Lepidoptera
  Pyralidae
  Phyticidae
  Pyraustidae
  Crambidae
  Tortricidae
  Galleriidae
  Lyonetiidae
  Yponomeutidae
  Pieridae
  Plutallidae
  Lymantriidae
  Noctuidae
Diptera
  Culicidae
  Simuliidae
  Tipulidae The compounds of formula I can be used along or together with suitable carriers and or additive materials. Suitable carriers and additive materials can be solid or liquid and correspond to the customary materials used in formulation technique, e.g. natural or regenerated materials, solvents, dispersing agents, wetting agents, adhesives, thickeners, binders and/or fertilisers.

The manufacture of agents according to the invention takes place in known fashion by intimate mixing and/or milling of active substances of formula I with suitable carriers, optionally with the addition of dispersing agents or solvents inert to the active substance.

The active substances can be present and be used in the following use forms:

Solid use forms:
dusting agents, spreading agents, granulates, coated granules, impregnated granules and homogeneous granules.

Liquid use forms:
a. Active substance concentrates dispersible in water: wettable powders, pastes, emulsions;
b. solutions.

For the manufacture of solid use forms (dusting agents, spreading agents) the active substances are mixed with solid carriers. As carriers there are, for example, kaolin, talcum, bolus, loess, chalk, limestone, limestone gravel, ataclay, dolomite, diatomaceous earth, precipitated silica, alkaline earth metal silicates, sodium and potassium aluminum silicates (feldspars and mica), calcium and magnesium sulphates, magnesium oxide, ground plastics materials, fertilisers such as ammonium sulphate, ammonium phosphate, ammonium nitrate, urea, ground vegetable products such as crop flour, bark flour, wood flour, nutshell flour, cellulose powder, residues from plant extraction, active carbon etc., each being usable per se or in admixture with others.

Granulates can be made very easily by dissolving an active substance according to Formula I in an organic solvent medium, applying the solution so obtained to a granulated material such as attapulgite, $SiO_2$, lime, bentonite etc. and then evaporating the organic solvent medium again.

Polymeric granulates can also be made by mixing the active substance of Formula I with polymerisable compounds (urea/formaldehyde, dicyandiamide/formaldehyde, melamine/formaldehyde or others) and then carrying out a careful polymerisation which does not affect the active substance, and wherein during the gel-forming stage, granulation is carried out. It is more favourable to impregnate preformed porous polymer granules (urea/formaldehyde, polyacrylonitrile, polyester and others) with a given surface area and favourably predetermined adsorption/desorption ratio with the active substance, e.g. in the form of a solution (in a low-boiling solvent) and then to remove the solvent. Such polymer granulates can be used in the form of microgranulates of bulk density of preferably 300 to 600 g/liter with the aid of dusting apparatus. Dusting can be carried out over extended surfaces of useful plant cultures with the aid of aircraft.

Granulates can also be obtained by compacting the carrier material with the active material and additive materials and then breaking up the compact.

These mixtures can furthermore contain additives stabilising the active substance and/or non-ionic, anion active or cation active materials, which, for example, improve the adherence of the active substance to plants and plant parts (adhesives and glues) and or guarantee better penetration (wetting agents) or dispersability (dispersing agents).

The following substances may, for example, be used: Olein-lime mixtures, cellulose derivatives (methyl cellulose, carboxymethyl cellulose), hydroxyethyleneglycol ethers of mono- and dialkyl phenols with 5-15 ethylene oxide groups per molecule and 8-9 carbon atoms in the alkyl group, lignin sulphonic acids, their alkali and alkaline earth salts, polyethylene glycol ethers (Carbowaxes), fatty alcohol polyglycol ethers with 5-20 ethylene oxide groups per molecule and 8-18 carbon atoms in the fatty alcohol part, condensation products of ethylene oxide, propylene oxide, polyvinyl pyrrolidone, polyvinyl alcohols, condensation products of urea-formaldehyde as well as latex products.

Active substance concentrates dispersible in water, i.e. wettable powders, pastes and emulsion concentrates are materials which can be diluted with water to any desired concentration. They consist of active agent, carrier, optionally additives stabilising the active substance, surface active agents and anti-foaming agents, and optionally solvents.

The wettable powders and pastes are obtained by mixing and/or milling to homogeneity the active substance with dispersing agents and powder form carriers in suitable apparatus. As carriers, for example the materials mentioned above for solid use forms can be used. In some cases, it is advantageous to use mixtures of various carriers. As dispersing agents there can be used, for example: condensation products of sulphonated naphthalene and sulphonated naphthalene derivatives with formaldehyde, condensation products of naphthalene or of naphthalene sulphonic acids with phenol and formaldehyde, as well as alkali, ammonium and alkaline earth metal salts of di-t-butyl-naphthalene sulphonic acids, fatty alcohol sulphates, such as salts of sulphonated hexadecanols, heptadecanols, octadecanols and salts of sulphated fatty alcohol glycol ethers, the sodium salt of oleyl methyl tauride, di-tertiary acetylene glycols, dialkyldilauryl ammonium chloride and fatty acid alkali and alkaline earth salts.

As anti-foaming agents, silicones may be used.

The active substances are so mixed with the above noted additives, milled, sieved and graded that for wettable powders the solid part has a particle size of 0.02 to 0.04 mm, and in the pastes does not exceed 0.03 mm. For the manufacture of emulsion concentrates and pastes dispersing agents as set forth in the preceding paragraphs are used, organic solvents and water. As solvents, there are, for example, alcohols, benzene, xylenes, toluene, dimethyl sulphoxide and mineral oil fractions boiling in the range 120° to 350° C. The solvent medium must be practically odourless, non-phytotoxic and inert with respect to the active substances.

Furthermore, the agents according to the invention can be used in the form of solutions. For this, one or more active substances of Formula I is dissolved in suitable organic solvents, solvent mixes or water. As organic solvent there can be used aliphatic and aromatic hydrocarbons, their chlorinated derivatives, alkyl naphthalenes, mineral oils, alone or in admixture with one another.

The content of active substance in the agents noted above lies between 0.02 and 95%, but it is to be noted that in application from aircraft or by means of other suitable application devices, concentrations of up to 99.5% or even pure active substance could be used.

The active substances of Formula I can, for example, be formulated as follows:

Dusting agent: for the manufacture of an (a) 5% and (b) 2% dusting agent, the following materials were used.

a. 5 parts active substance 95 parts talcum
b. 2 parts active substance 1 part highly disperse silica 97 parts talcum.

The active substances were mixed with the carrier materials and milled.

Granulate: for manufacturing a 5% granulate, the following materials were used:
5 parts active substance
0.25 parts epichlorohydrin
0.25 parts cetyl polyglycol ether
3.50 parts polyethylene glycol ("Carbowax")
91 parts kaolin (particle size 0.3–0.8 mm).

The active substance was mixed with epichlorohydrin and dissolved in 6 parts acetone, whereafter the polyethylene glycol and cetyl polyglycol ether were added. The solution thus obtained was sprayed onto kaolin and the acetone then evaporated in vacuo.

Wettable powder: for manufacturing an (a) 40%, and (b) and (c) 25% and (d) 10% wettable powder, the following components were used:
a. 40 parts active substance
 5 parts lignin sulphonic acid, sodium salt
 1 part dibutyl naphthalene sulphonic acid, sodium salt
 54 parts silica;
b. 25 parts active substance
 4.5 parts calcium lignosulphonate
 1.9 parts champagne chalk-hydroxyethyl cellulose mixture (1:1)
 1.5 parts sodium dibutyl naphthalene sulphonate
 19.5 parts silica
 19.5 parts champagne chalk
 28.1 parts kaolin.
c. 25 parts active substance
 2.5 parts isooctylphenoxy-polyoxyethylene-ethanol
 1.7 parts champagne chalk-hydroxyethyl cellulose mix (1:1)
 8.3 parts sodium aluminium silicate
 16.5 parts kieselguhr
 46 parts kaolin.
d. 10 parts active substance
 3 parts mixture of sodium salts of fatty alcohol sulphates
 5 parts naphthalene sulphonic acid formaldehyde condensate
 82 parts kaolin.

The active substances were intimately mixed in suitable mixers with the additive materials and milled on suitable mills and rolls. Wettable powders were obtained which could be diluted with water to suspensions of any desired concentration.

Emulsifiable concentrate: for manufacturing an (a) 10% and (b) 25% emulsifiable concentrate, the following materials were used:
a. 10 parts active substance,
 3.4 parts epoxidised vegetable oil,
 13.4 parts of a combination emulsifier consisting of fatty alcohol polyglycol ethers and calcium alkyl aryl sulphonates
 40 parts dimethylformamide
 43.2 parts xylene.
b. 25 parts active substance acid ester
 2.5 parts epoxidised vegetable oil
 10 parts of an alkyl aryl sulphonate-fatty alcohol polyglycol ether mixture
 5 parts dimethylformamide
 57.5 parts xylene.

Emulsions of any desired concentration could be made from these concentrations by dilution with water.

Spraying agent: for making a 5% spraying agent the following components were used:

5 parts active substance
1 part epichlorohydrin
94 parts petrol (boiling range 160°–190° C). The materials described can also be mixed with other biocidally active substances or agents. Thus, the new agents can contain, apart from the noted compounds of general formula I, for example, insecticides for broadening the spectrum of activity.

The following examples will serve to illustrate the invention

EXAMPLE 1

1a. 21.7g 1-bromo-3,7-dimethyl-2,6-octadiene was added to a solution of 15.2g 4-propargyloxyphenyol (boiling point 92°–93° C/0.04 torr $n_D^{20}$ : 1.5625) in 150 ml pure 1,2-dimethoxyethane, and immediately thereafter with stirring at 20°–22° C a solution of 6.4g 85% potassium hydroxide in 100 ml absolute ethanol was added dropwise. The addition of potassium hydroxide solution (lasting about 8 hours) was so regulated that the reaction mixture always remained weakly alkaline (pH about 8–9). After the addition of the base the mixture was stirred further for 16 hours at room temperature and then warmed for one hour to 70° C and thereafter cooled and filtered from the precipitated potassium bromide. The filtrate was reduced to about 50 ml, takenup in a diethyl ether hetane mixture (1:4) washed 3 times with 30 ml 10% aqueous potassium hydroxide and then washed neutral with water. The organic phase was dried over sodium sulphate and the solvent distilledoff in vacuum. The remaining (4-propargyloxy)phenoxy-3,7,dimethyl-2,6-octadiene was purified by chromatography on silica gel (activity III) with an ether hexane mixture (1:5) $n_D^{20}$ 1.53156. This ether can also be purified by high vacuum distillation.

Analogously to example 1a), from 3-propargyloxyphenol (B.pt. 84°–85°C/0.02 torr; $n^D 20$ 1.5640) and 1-bromo-3,7-dimethyl-2, 6-octadiene the 1-(3-propargyloxy)phenoxy-3,7-dimethyl-2,6-octadiene ($n_D^{20}$ 1.5326) can be prepared, as well as 1(4-propargyloxy)-phenoxy-3,7-dimethyl-2,6-nonadiene ($n_D^{20}$ : 1.5301) from 4-propargyloxyphenol and 1-bromo-3,7-dimethyl 2,6-nonadiene.

The 4-propargyloxyphenol used for the manufacture of 1-(4-propargyloxy)phenoxy-3,7-dimethyl-2,6-octadiene can be manufactured in the following fashion: 165 g of propargylchloride were added dropwise with stirring and within 2 hours to a mixture of 220 g hydroquinone, 305 g anhydrous potassium carbonate, 7.3 g finely divided potassium iodide and 700 ml acetone, under a nitrogen atmosphere at the boiling temperature of acetone. Thereafter the mixture was boiled under reflux for a further 14 hours. The reaction mixture was then diluted with 800 ml acetone, filtered clear and the filtrate reduced. The residue was taken up in 1500 ml toluene and the toluene solution was repeatedly washed with 200 ml each time of warm water at 40°–50° C. After drying the toluene solution over sodium sulphate and the addition of some active carbon the mixture was filtered, the filtrate freed from the solvent in vacuo and the residue dissolved in 1000 ml ether. The ether solution was washed three times with 200 ml 30% ice-cold caustic soda and thereafter twice with water. The purified aqueous alkali phases were then washed again twice with a little ether. The aqueous alkaline phase which contained the sodium salt of 4-propargyloxyphenol was now allowed to flow with vigorous stirring to a mixture of 100 ml chloroform, 1 kilogram ice and 600 ml concentrated hydrochloric acid. The phases were separated, the aqueous hydrochloric acid phase subsequently washed once with chloroform, the purified chloroform phase washed briefly with water, dried over sodium sulphate and the solvent distilled off. The residue was then fractionally distilled in vacuum by means of which the colourless 4-propargyloxyphenol of boiling point 92°–93° C/0.04 torr was obtained.

1b. 9.6 g propargylbromide were added dropwise within 30 minutes to a mixture of 16.4g 1-(4-hydroxy)-phenoxy-3,7-dimethyl-2,6-octadiene and 13.8 g anhydrous potassium carbonate in 70 ml acetone at the boiling temperature of the acetone and under a nitrogen atmosphere. After the addition of the propargyl bromide, the mixture was heated for a further 8 hours under reflux. For finishing the mixture was filtered from the solids, the filter residue repeatedly washed out with diethyl ether and the filtrate freed in vacuum from the solvents. The oily residue was taken up in diethylether hexane (1:4), washed three times with 10% caustic potash and then with water. After drying the organic phase over sodium sulphate and sucking off the solvent in vacuo, the 1-(4-propargyloxy)phenoxy-3,7-dimethyl-2,6-octadiene was further purified as given under paragraph a). $n_D^{20}$ :1.5315.

The 1-(4-hydroxy)phenoxy-3,7-dimethyl-2,6-octadiene used as a starting product in Example 1 (b) can be manufactured as follows: to a solution of 165 g hydroquinone in 2000ml 1,2-dimethoxyethane there was added with stirring and evenly at room temperature from two dropping funnels within ten hours 326 g 1-bromo-3,7-dimethyl-2,6-octadiene and a solution of 95 g about 90% potassium hydroxide in 1200 ml absolute ethanol, and in such a fashion that the reaction mixture always reacted slightly alkaline. Thereafter stirring was continued for 5 hours at room temperature and 3 hours at 50° C. The whole reaction was carried out under a nitrogen atmosphere.

For finishing, after cooling of the reaction mixture it was filtered from the precipitated potassium bromide, the solvent removed in vacuum, and the residue taken up in 1600 ml n-hexane and extracted four times with about 200 ml 20% aqueous caustic potash. The purified aqueous alkali phases were then washed twice with a little n-hexane. Then the aqueous alkali solution was diluted with about 1500 ml water and exhaustively extracted with diethyl ether. The purified ethereal extracts were washed with a very little water, dried over sodium sulphate and the ether distilled off. The remaining 1-(4-hydroxy)phenoxy-3,7-dimethyl-2,6-octadiene which crystallized after a little time was distilled in vacuo for further purification (boiling point 140°–142° C/0.05 torr) and then crystallized from pentane. Melting point 45°–57° C.

1c. To a solution of 5.77 g 1-(4-propargyloxy)-phenoxy-3,7-dimethyl-2,6-octadiene in 55 ml dichloromethane there was added at −2° to 0° C with stirring a solution of 4.1g 86% m-chloroperbenzoic acid in 40 ml of a dichloremethane ether mixture (9:1), dropwise within 4 hours. After a further 14 hours stirring at 0° to 2° C the reaction mixture was diluted with n-hexane, washed three times at about 5° C with 40 ml 10% aqueous caustic potash and then washed neutral with water. After drying the organic phase over sodium sulphate the solvent was distilled off in vacuum and the product chromatographically purified on silica gel (activity 3) (elutriation agent: diethyl ether hexane 1:3) by means of which pure colourless 1-(4-propargyloxy)phenoxy-6,7-epoxy-3,7-dimethyl-2-octene was obtained. $n_D^{20}$ : 1,5263.

EXAMPLE 2

A mixture of 18.7 g 1-bromo-3,7-dimethyl-6-octene, 11.2 g 4-propargyloxyphenol, 12 g anhydrous powdered potassium carbonate, 1g finely powdered potassium iodide and 60 ml methylethylketone was stirred for 48 hours reaction mixture was filtered off, the filtrate reduced, then treated with 300 ml n-hexane, the solution washed three times with 10% ice-cold caustic potash and then washed neutral with water. After drying the organic phase over sodium sulphate the solvent was distilled off in vacuo and the 1-(4-propargyloxy)-phenoxy 3,7-dimethyl-6-octene chromatographically purified on silica gel. Elution agent: diethylether hexane (1:10). $n_D^{20}$ : 1,5142.

The so obtained 1-(4-propargyloxy)-phenoxy-3,7-dimethyl 6-octene can be transferred with 3-chloroperbenzoic acid in fashion similar to that in example 2 into the 1-(4-propargyloxy) phenoxy-6,7-epoxy-3,7-dimethyloctene. ($n_D^{20}$ : 1.5115).

In a fashion similar to examples 1–2, the following compounds were also manufactured:

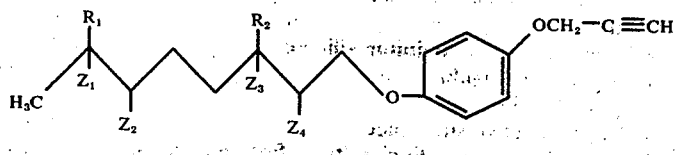

(C≐C— means a carbon carbon bond; —O— means an oxygen bridge).

| $R_1$ | $R_2$ | $Z_1; Z_2$ | $Z_3; Z_4$ | Physical data |
|---|---|---|---|---|
| $C_2H_5$ | $CH_3$ | —C—C— | —C—C— | $n_D^{20} = 1,5301$ |
| $C_2H_5$ | $CH_3$ | —O— | —C—C— | $n_D^{20} = 1,5245$ |
| $CH_3$ | $CH_3$ | —C—C— | $Z_3 = H; Z_4 = H$ | $n_D^{20} = 1,5143$ |
| $CH_3$ | $CH_3$ | —O— | $Z_3 = H; Z_4 = H$ | $n_D^{20} = 1,5115$ |
| $CH_3$ | $CH_3$ | $Z_1 = H; Z_2 = H$ | $Z_3 = H; Z_4 = H$ | $N_D^{20} = 1,5003$ |
| $C_2H_5$ | $CH_3$ | $Z_1 = H; Z_2 = H$ | $Z_3 = H; Z_4 = H$ | $n_D^{20} = 1,4981$ |
| $C_2H_5$ | $CH_3$ | —C—C— | $Z_3 = H; Z_4 = H$ | |
| $C_2H_5$ | $CH_3$ | —O— | $Z_3 = H; Z_4 = H$ | |

EXAMPLE 3

10 larvae of Dysdercus fasciatus, which were 8–10 days before the adult moult, were topically treated with acetonic active substance solutions. The test animals were then kept at 28° C and 80–90% relative humidity. As food, the Dysdercus fasciatus larvae had groats from preswollen cotton seeds.

After about 10 days, i.e. as soon as the control animals had completed their adult moult, the test animals were evaluated. Apart from normal adults and dead larvae special forms were to be found such as extra larvae (larvae with an additional larval skin) and adultoids (adults with larval features). In the special types it is a question of non-viable stages of developments which are not to be found in the normal cycle of development.

From the following table the number of normal adults is evident which were to be found at the various concentrations given:

| Compound | Amount of Active Substance in γ | Dysdercus fasciatus |
|---|---|---|
| 1-(4-Propargyloxy)-phenoxy-6,7-epoxy-3,7-dimethyl-2-octene | 5 | 0 |
|  | 0,5 | 1 |
| 1-(4-Propargyloxy)-phenoxy-6,7-epoxy-3,7-dimethyl-2-nonene | 5 | 0 |
| 1-(4-Propargyloxy)-phenoxy-6,7-epoxy-3,7-dimethyl-octane | 5 | 0 |
|  | 0,5 | 0 |
| Control | — | 10 |

EXAMPLE 4

In each test 10 fresh pupae of Dermestes lardarius were topically treated with solutions of active substance in acetone. The pupae were then kept at 28° C and 80–90% relative humidity.

After about 10 days, i.e. as soon as the control animals had left the pupal casing as Imagines, the test animals were evaluated; as well as normal adults and dead pupae adultoids (adults with larval characteristics) were found.

The adultoids were not viable stages of development and they are not to be found in the normal cycle of development. In the following table the number of normal adults is given which were to be found at the various concentrations given.

| Compound | Amount of Active Substance in γ | Dermestes lardarius |
|---|---|---|
| 1-(4-Propargyloxy)-phenoxy-6,7-epoxy-3,7-dimethyl-2-octene | 5 | 0 |
|  | 0,5 | 1 |
| 1-(4-Propargyloxy)-phenoxy-6,7-epoxy-3,7-dimethyl-2-nonene | 5 | 0 |
|  | 0,5 | 0 |
| 1-(4-Propargyloxy)-phenoxy-6,7-epoxy-3,7-dimethyl-octane | 5 | 1 |
| Control | — | 10 |

EXAMPLE 5

In each case 10 fresh pupae of Tenebrio molitor were topically treated with active substance solutions in acetone. The pupae were then kept at 28° C and 80–90% relative humidity. After about 10 days, i.e. as soon as the control animals had left the pupal skin as Imagines, the test animals were evaluated. As well as normal adults and dead pupae, adultoids were found (adults with larval features).

The adultoids were not viable stages of developments and they are not to be found in the normal cycle of development.

In the following table the number of normal adults is given which were to be found at the various concentrations given.

| Compound | Amount of Active Substance in γ | Tenebrio molitor |
|---|---|---|
| 1-(4-Propargyloxy)-phenoxy-3,7-dimethyl-2-nonene | 5 | 0 |
|  | 0,5 | 0 |
| 1-(4-Propargyloxy)-phenoxy-6,7-epoxy-3,7-dimethyl-2-octene | 5 | 0 |
|  | 0,5 | 0 |
| Control | — | 10 |

EXAMPLE 6

10 fresh pupae each of Leptinotarsa decemlineata were topically treated with solutions of active substance in acetone. The pupae were then kept at 28° and 80–90% relative humidity.

After about 10 days i.e. as soon as the control animals had left the pupal casing as imagines, the test animals were evaluated. As well as normal adults and dead pupae, adultoids were found (adults with larval features). In the case of adultoids they are not viable stages of development and are not to be found in the normal cycle of developments.

In the following table the number of normal adults is given which were to be found at the various concentrations given.

| Compound | Amount of Active Substance in γ | Leptinotarsa decemlineata |
|---|---|---|
| 1-(4-Propargyloxy)-phenoxy-6,7-epoxy-3,7-dimethyl-2-octene | 5 | 0 |
|  | 0,5 | 0 |
| Control | — | 10 |

What we claim is:

1. A compound of the formula

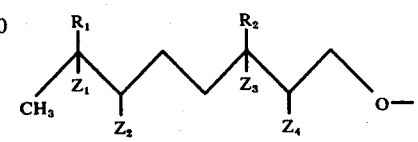
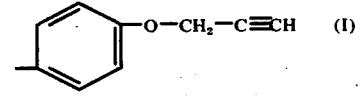

(I)

wherein
$Z_1$ and $Z_2$ together are an oxygen bridge,
$R_1$ and $R_2$ are each methyl or ethyl, and
$Z_3$ and $Z_4$ together form a carbon-carbon-bond or are each hydrogen 2. A compound according to claim 1 of the formula

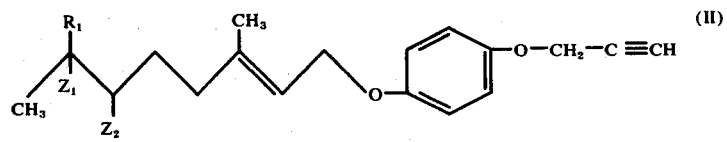

(II)

wherein
$R_1$ is methyl or ethyl and
$Z_1$ and $Z_2$ together are an oxygen bridge.

3. The compound according to claim 2 which has the formula

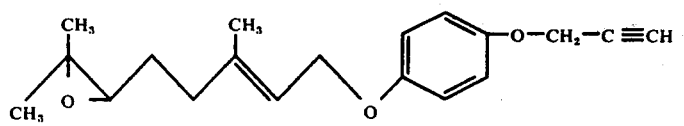
4. The compound according to claim 2 which has the formula
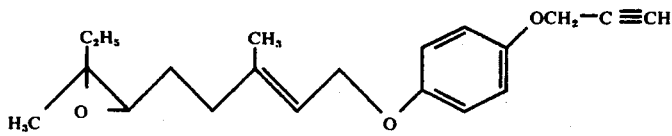
5. The compound according to claim 1 which has the formula
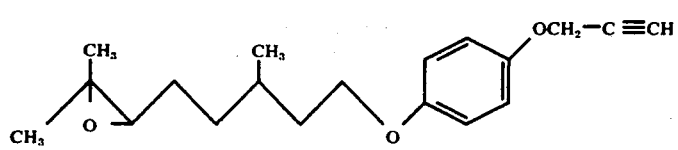
6. The compound according to claim 1 of the formula
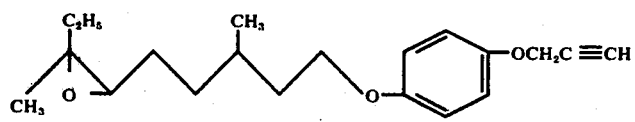
* * * * *